United States Patent
Sakaide et al.

[11] Patent Number: 5,892,581
[45] Date of Patent: Apr. 6, 1999

[54] ABSORPTIVITY DETECTING APPARATUS, CHROMATOGRAPHIC APPARATUS, METHOD OF DETECTING ABSORPTIVITY AND METHOD OF CHROMATOGRAPHY

[75] Inventors: Toshihiko Sakaide; Masahito Ito; Yoshio Fujii; Shigeru Matsui, all of Hitachinaka, Japan

[73] Assignee: Hitachi, Ltd., Tokyo, Japan

[21] Appl. No.: 936,242

[22] Filed: Sep. 24, 1997

[30] Foreign Application Priority Data

Sep. 27, 1996 [JP] Japan .................................. 8-255811

[51] Int. Cl.$^6$ .................................................. G01N 21/33
[52] U.S. Cl. .................................... 356/344; 356/319
[58] Field of Search .................... 356/344, 319, 356/436

[56] References Cited

U.S. PATENT DOCUMENTS

| | | |
|---|---|---|
| 3,897,154 | 7/1975 | Hawes ...................................... 356/323 |
| 4,411,519 | 10/1983 | Tagami . |
| 4,449,821 | 5/1984 | Lee .......................................... 356/319 |
| 5,026,992 | 6/1991 | Wong . |
| 5,042,948 | 8/1991 | Fletcher .................................... 356/328 |
| 5,262,645 | 11/1993 | Lambert et al. . |
| 5,327,356 | 7/1994 | Lang et al. . |

FOREIGN PATENT DOCUMENTS 3-226632  7/1991  Japan .

*Primary Examiner*—Richard A. Rosenberger
*Attorney, Agent, or Firm*—Kenyon & Kenyon

[57] ABSTRACT

In order to suppress base line drift due to change in a light source and to start analysis with a short waiting time so as to improve quantitative accuracy of analysis, a detected signal in a measurement wavelength and a detected signal in a reference wavelength are measured at each of arbitrary light intensity points by varying light intensity of a light source, and the corresponding relationship between the wavelengths is stored. An incident light intensity of the measurement wavelength is estimated from a detected signal in the reference wavelength based on the stored data.

7 Claims, 5 Drawing Sheets

ABSORPTIVITY DETECTING APPARATUS, CHROMATOGRAPHIC APPARATUS, METHOD OF DETECTING ABSORPTIVITY AND METHOD OF CHROMATOGRAPHY

BACKGROUND OF THE INVENTION

The present invention relates to an absorptivity detecting apparatus, a chromatographic apparatus, a method of detecting absorptivity and a method of chromatography.

Many absorptivity detecting apparatuses are used as detectors for liquid chromatographic apparatuses. The absorptivity detecting apparatus utilizes a phenomenon that a sample absorbs light having a specific wavelength, and detects characteristics of the ample by detecting a quantity of absorbed light of the specific wavelength (hereinafter referred to as "sample measurement wavelength"). That is, a quantity of a sample or the like is detected by comparing an intensity of incident light and an intensity of transmitted light. Such a technology is disclosed, for example, in Japanese Patent Application Laid-Open No. 3-226632.

In such a technology, it is known that an intensity of light emitted from a light source does not agree with an intensity of light incident to a sample. The reason is that light suffers effects such as change of refractive index and so on when the light is passing through the sample and passing through each element of an optical system. Therefore, by utilizing light having a wavelength which is less absorbed in the sample (hereinafter referred to as "reference wavelength"), an absorptivity is detected by comparing a detected value for the reference wavelength and a detected value for a detecting wavelength.

However, it has been found that absorptivity cannot be measured accurately unless the light source and the light intensity are stabilized. In general, it takes a long time to stabilize an intensity of a light source. Further, after stabilized, small change in light intensity of the light source cannot be inevitable. For example, measurement is continuously performed for several minutes to several hours at longest in a liquid chromatographic apparatus, and therefore an effect due to change in light intensity of the light source becomes large.

SUMMARY OF THE INVENTION

An object of the present invention is to provide an absorptivity detecting apparatus, a chromatographic apparatus, a method of detecting absorptivity and a method of chromatography which are capable of maintain a detecting accuracy even if light intensity of a light source is changed.

Before describing the detailed means to solve the problem, intention of the inventors will be described first. The inventors found that radiant spectrum is changed when a light intensity of a light source changes, and this change affects on the detection accuracy. That is, temperature of the light source is changed, and light intensity change ratio between wavelengths becomes different. Explaining more detailed, when light intensity of the light source, change in light intensity of the sample measurement wavelength does not always agree with change in light intensity of the reference wavelength. By the difference of the light intensity change ratio between the wavelengths, so-called base line drift occurs and accordingly the absorptivity cannot be detected accurately.

In order to solve the problem, the apparatus of the present invention is constructed so as to irradiate light from a light source for emitting light containing at least a first wavelength (sample measurement wavelength) and a second wavelength (reference wavelength) on a sample, obtain a correction value for correcting change in spectral distribution caused by change in light intensity of the light source, and obtain an absorptivity based on the correction value, a detected value by light of the first wavelength and a detected value by light of the second wavelength.

By constructing as described above, even if the light intensity change ratio between the measurement wavelength and the reference wavelength becomes different from each other due to change in the light intensity of the light source, correction can be performed by the correction value and accordingly the absorptivity can be detected accurately.

DETAILED DESCRIPTION OF THE INVENTION

Figure 2:
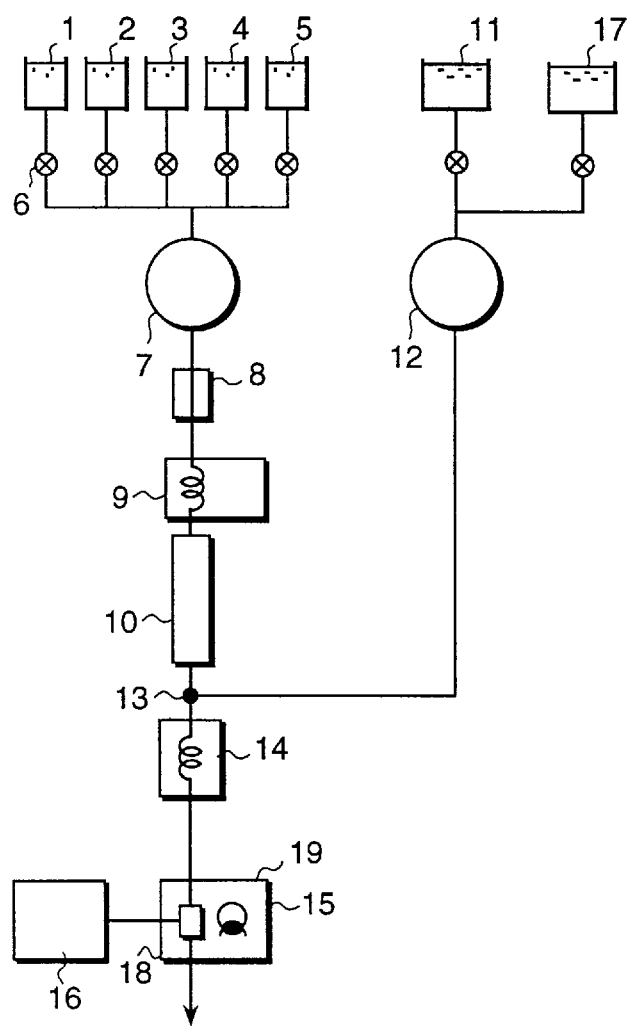
FIG. 2 is a diagram showing the overall construction of a chromatographic apparatus.

An embodiment of the present invention will be described below, referring to the accompanying drawings. FIG. 2 is a diagram showing the overall construction of a chromatographic apparatus (an amino acid analyzer). Any one of buffer solutions 1 to 4 and a column reprocessed solution 5 is selected by an electromagnetic valve series 6. The selected buffer solution 1 to 4 (or the reprocessed solution 5) is pumped by a buffer solution pump 7 to be supplied to an auto-sampler 9 through an ammonia filter column 8. After mixing an amino acid sample by the auto-sampler 8, the mixed solution is separated by a separation column 10. On the other hand, a ninhydrin reagent 11 and a ninhydrin buffer solution 17 are mixed and the mixed solution is pumped by a ninhydrin pump 12 to be supplied to a mixer 13. In the mixer, the separated sample and the ninhydrin reagent 11 are mixed, and reaction is accelerated by a reaction coil 14 to be colored. The colored amino acid is supplied to a flow cell 18 in a photometer 15. In the flow cell, light from a light source 19 passes through the colored amino acid, and the passed light is detected and processed by a data processor 16 to be output (displayed) as a chromatogram and to be recorded and stored.

Figure 3:
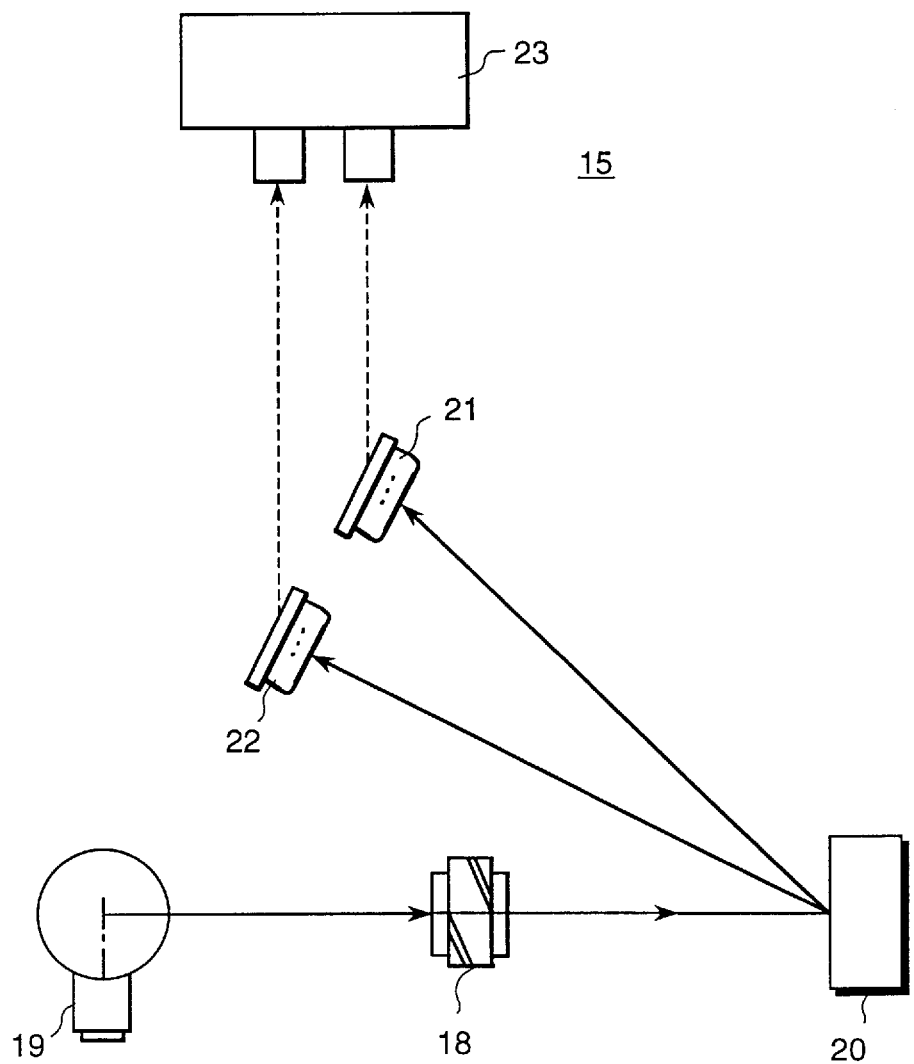
FIG. 3 is a view explaining detail of a detector.

The photometer 15 will be described below in detail, referring to FIG. 3. White light emitted from the light source 19 is incident onto the flow cell 18. Light having a wavelength near 570 nm in the incident white light is absorbed by the colored amino acid flowing in the flow cell 18, and the intensity of the incident white light is weakened. The white light weakened by the absorption is separated into light in each wavelength by a grating 20, and a light intensity $I_t$ (570 nm) of the sample measurement wavelength (wavelength affected by effect of absorption of the sample, 570 nm in this embodiment) and a light intensity $I_t$ (700 nm) of the reference wavelength (wavelength not affected by effect of absorption of the sample, 700 nm in this embodiment) are detected. Detected signals of the sample measurement wavelength and the reference wavelength are transmitted to a computer 23 to output an absorptivity. In this case, the absorptivity can be also obtained using a sample wavelength of 440 nm instead of 570 nm.

In detail, based on a transmitted light intensity $I_t$ (700 nm) of 700 nm, the absorptivity A (570 nm) is obtained as follows. This will be described, referring to FIG. 1. An absorptivity is obtained by transforming $I_t$ (700 nm) to $I_i$ (570 nm) using an arbitrary function. That is, the following transformation is executed, $$I_i(570\ nm) = f\{I_t(700\ nm)\} \qquad \text{Equation 1}$$

and then calculation is performed using the following equation.

$$A(570\ nm) = -\log_{10}[\{I_t(570\ nm)/f\{I_t(700\ nm)\}\}] \qquad \text{Equation 2}$$

The following can be chosen as the function f(x).
① Linear equation:

$$f(x) = ax + b \qquad \text{Equation 3}$$

When b≠0, a linear transformation not pass through the point of origin can be performed.
[0014]
② Quadratic equation:

$$f(x) = ax^2 + bx + c \qquad \text{Equation 4}$$

A curved line can accurately express the relationship.
[0016]
③ Higher polynomial (expression of higher than the third order):

$$f(x) = ax^n + bx^{n-1} + cx^{n-2} + \qquad \text{Equation 5}$$

The relationship can be expressed more detailed.

The absorptivity A(570 nm) of sample measurement wavelength 570 nm is expressed by the following Equation 6.

$$A(570\ nm) = -\log_{10}[\{I_t(570\ nm)/I_i(570\ nm)\}] \qquad \text{Equation 6}$$

where $I_t$ (570 nm) is intensity of transmitted light and $I_i$ (570 nm) is intensity of incident light. Essentially, the same wavelength is used for $I_t$ (570 nm) and $I_i$ (570 nm).

An embodiment of absorptivity detection by two-wavelength (sample measurement wavelength of 570 nm and reference wavelength of 570 nm) will be described below.

Figure 4:
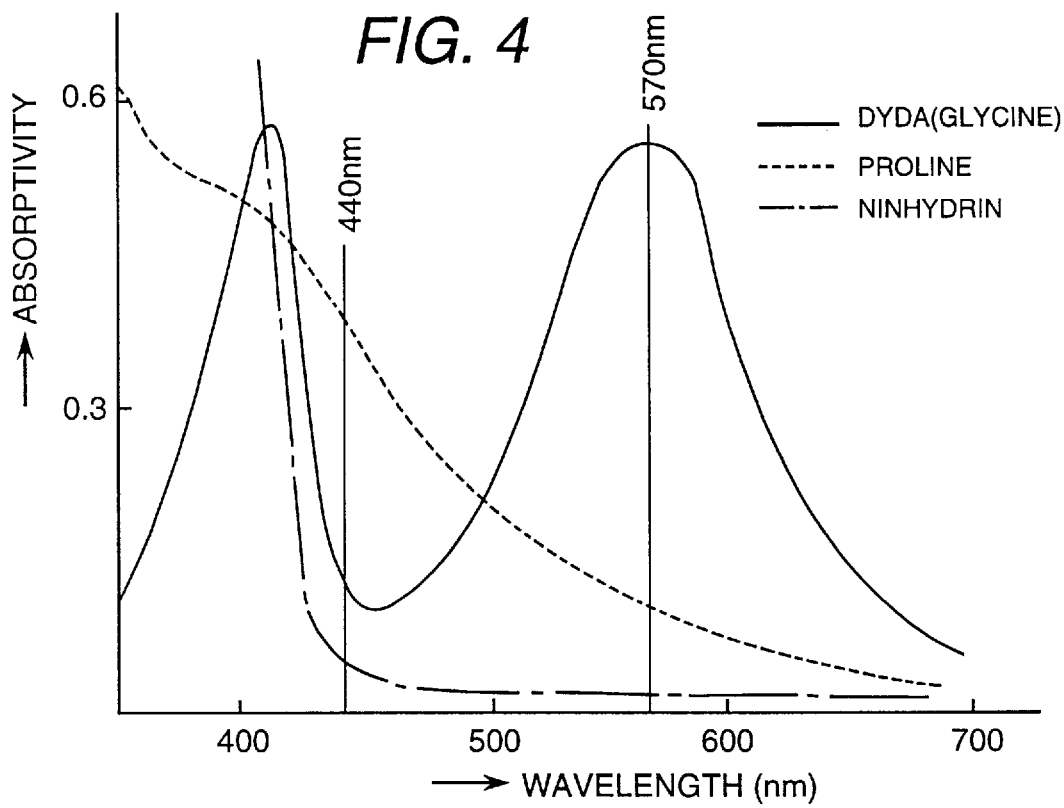
FIG. 4 is a graph showing absorptivity versus wavelength.

FIG. 4 is shows absorptivity versus wavelength. As shown in FIG. 4, light having a wavelength of 570 nm is absorbed by a sample, but light having a wavelength of 700 nm is hardly absorbed by the sample. That is, the light having a wavelength of 700 nm is hardly absorbed by the sample, but only the effect of refractive index on the light having a wavelength of 700 nm is nearly equal to that on the light having a wavelength of 700 nm. Further, size of a light image cut by a slit or a mask and a light path transmitted through a lens and a grating are the same in the light having a wavelength of 700 nm and in the light having a wavelength of 700 nm. Therefore, it can be simply assumed that an intensity of the transmitted light of 700 nm is proportional to an intensity of the incident light of 570 nm.

Description will be made on the reason why $I_i$ (570 nm) is obtained by transforming from $I_t$ (700 nm) as described above. Essentially, intensities in the same wavelength should be used in $I_t$ (570 nm) and $I_i$ (570 nm). However, in the flow cell of the detector, there actually occur not only change of absorptivity but also change of refractive index. In addition to this, it is difficult to really measure an intensity of light incident to the flow cell before being incident to the flow cell. Because of the two reasons, an intensity of the reference light (700 nm in this embodiment) different from the wavelength of light passing through the flow cell is used instead of the intensity of the incident light.

Figure 5:
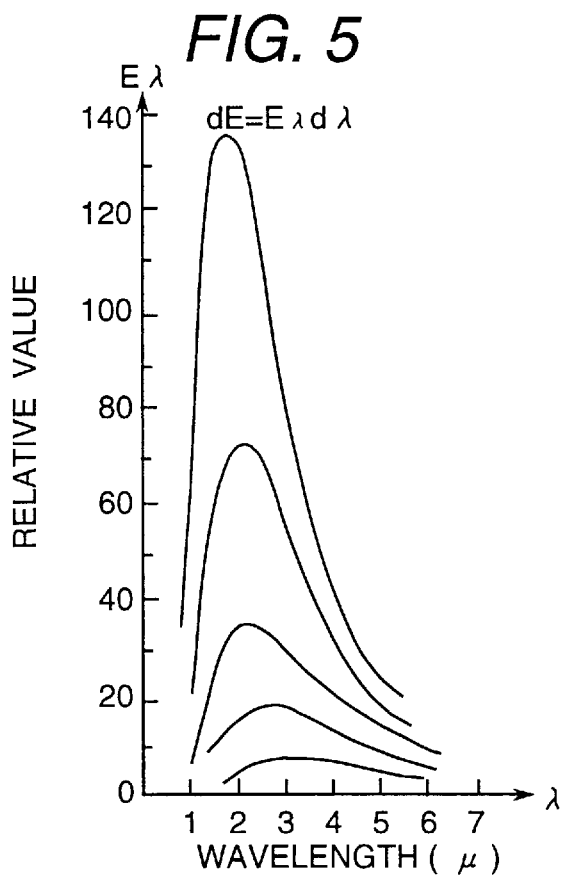
FIG. 5 is a graph showing relative value of wavelength.
Figure 6:
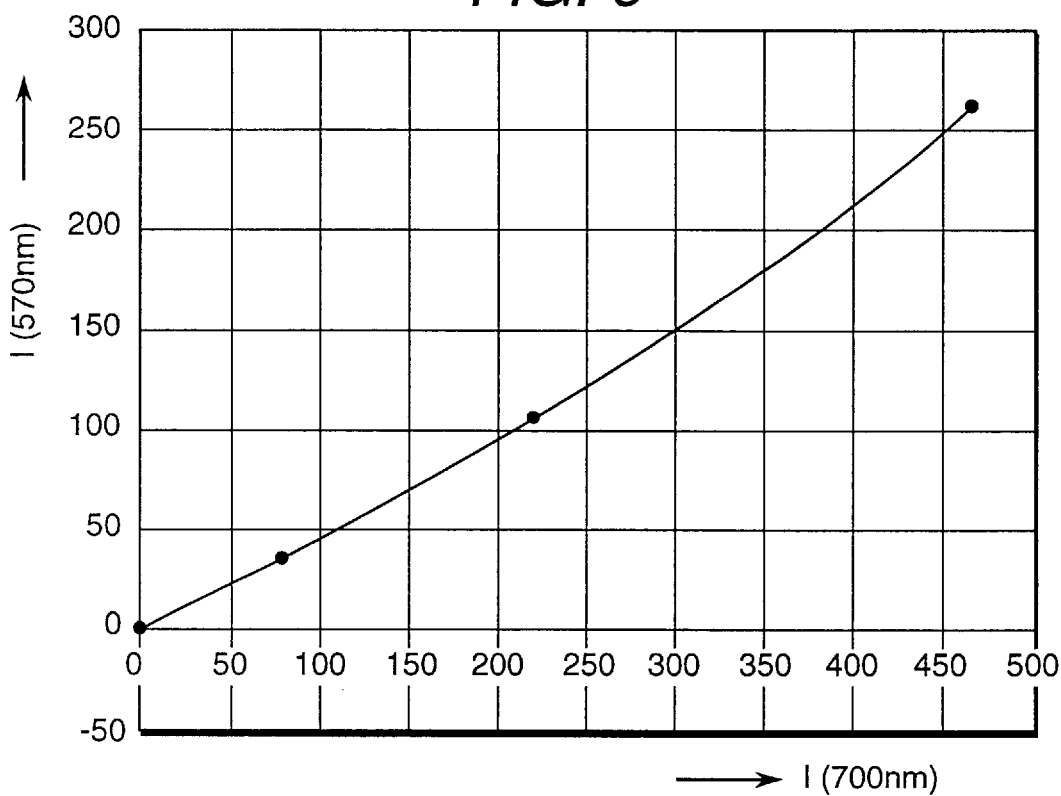
FIG. 6 is a graph showing a correlation between measurement wavelength (570 nm) and reference wavelength (700 nm).
Figure 7:
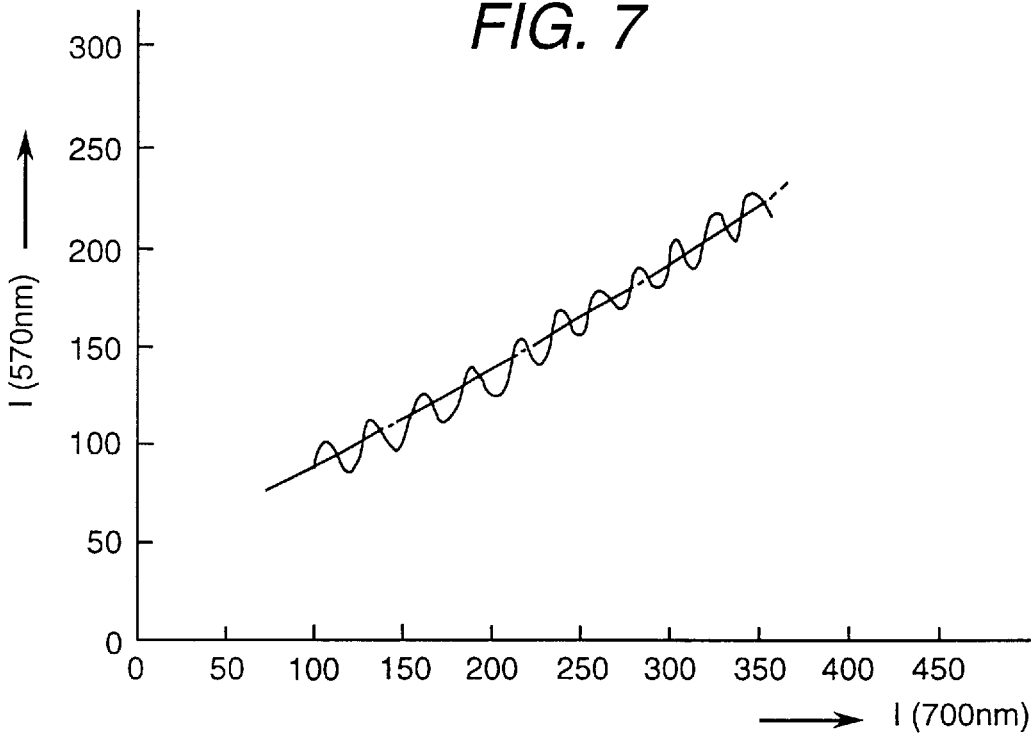
FIG. 7 is a graph showing change of refractive index.

On the other hand, as shown in FIG. 5, the relative value $E_\lambda$ varies to the wavelength. In more detail, FIG. 6 shows an example of detection for wavelength 570 nm and wavelength 700 nm. That is, the intensity change ratio of the reference wavelength and the intensity change ratio of the measurement wavelength due to intensity change of the light source are not in a proportional relationship. Therefore, when the intensity of the light source is changed, the absorptivity is changed and base drift occurs by the difference of change ratios between wavelengths to the change in the light source even if the sample absorptivity in the flow cell does not change.

Therefore, by obtaining the relationship between the intensity change ratio of the reference wavelength and the intensity change ratio of the measurement wavelength due to intensity change of the light source as shown in FIG. 6, coefficients shown in Equation 3, Equation 4 or Equation 5 are calculated using the minimum square method.

The coefficients in Equation 3, Equation 4 or Equation 5 can be calculated by the following methods ①~③.
① Planck's black body radiation law:
It is essential that the correlation of change between $I_i$ (570 nm) and $I_t$ (570 nm) is obtained as variable parameter of temperature using Planck's black body radiation law.
② Actual measurement (neglecting refractive index):
The coefficients can be obtained from an actual measurement other than from a model. When the coefficient are obtained from an actual measurement, correction from the black body radiation model can be performed and accordingly it is possible to reflect an actual optical system. For example, in a case of using a halogen lamp such as an iodine lamp, it is preferable to use actual measured values. A method of measurement is that a flow cell is filled with air or water and the fluid is stilled to eliminate change of the refractive index. Then, temperature of a light source is varied by changing voltage applied to the light source.

The resultant intensities of transmitted light for the two wavelengths are plotted to the abscissa and the ordinate respectively as shown in FIG. 6. A transform function can be obtained from the plotted graph (FIG. 6) by regressing to a linear equation, a quadratic equation or a higher polynomial. In detail, each of the coefficients in Equation 3 to Equation 5 are calculated by storing each of the plots in the computer 23 and executing calculation processing in a CPU in the computer 23.

③ Actual measurement (taking refractive index into consideration):
In the method of measuring $I_t$ (570 nm) and $I_t$ (700 nm), change of refractive index does not occur since the air or the water in the flow cell is stilled. Equation 3, Equation 4 or Equation 5 can be used for the method taking refractive index into consideration. In this case, while the voltage applied to the light source is kept constant (that is, temperature of the lamp is kept constant), the pump 7 and the pump 12 of the amino acid analyzer are operated to feed the eluting solvent and the reaction solution into the flow cell. Since no sample is injected in this state, this measurement corresponds to measuring a base line. Therein, when plots of the relationship between $I_t$ (570 nm) and $I_t$ (700 nm) is measured, change in the absorptivity and change in the refractive index of the solution are reflected on the plots. Actually, the change in absorptivity of $I_r$ (570 nm) is not reflected on the change in $I_t$ (700 nm), but the change in the refractive index is mainly drawn as a fitting curve of the plotted graph. This fitting curve can be used as a function f(x).

Further, it is also possible that only change in the refractive index is measured without change in the absorptivity by feeding only the ninhydrin buffer solution 17 by removing ninhydrin component from an actual reaction solution to be fed by the pump.

Figure 8:
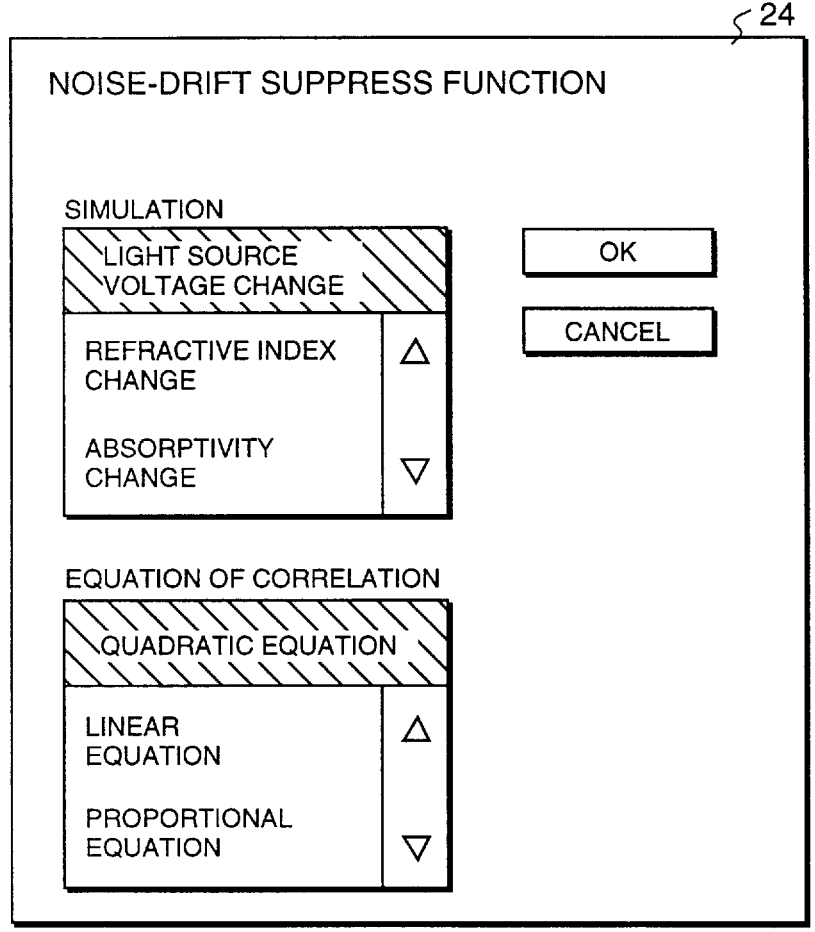
FIG. 8 is a view showing a screen of a computer display.

Description will be made below on another embodiment which is operated according to a computer screen 24 of a data processing apparatus 16 as shown in FIG. 8. A user can operate noise-drift suppress function according to the screen 24 using installed functions of this apparatus. Firstly, a type of simulation is selected and "OK" button is touched. Then the computer 23 operates as the following cases ①–③.

① A case of selecting light source voltage change:

The flow cell 18 of the photometer 15 is fed and filled with only the first buffer solution 1 using the pump 7. Then, voltage applied to the light source 19 is automatically varied from 11V to 13V in one minute. A plotted graph (FIG. 6) of intensity of the reference wavelength light versus intensity of sample wavelength light at that time is formed, and regression coefficients are obtained by regressing to the quadratic equation (Equation 4). Thus, the operation is completed.

Figure 1:
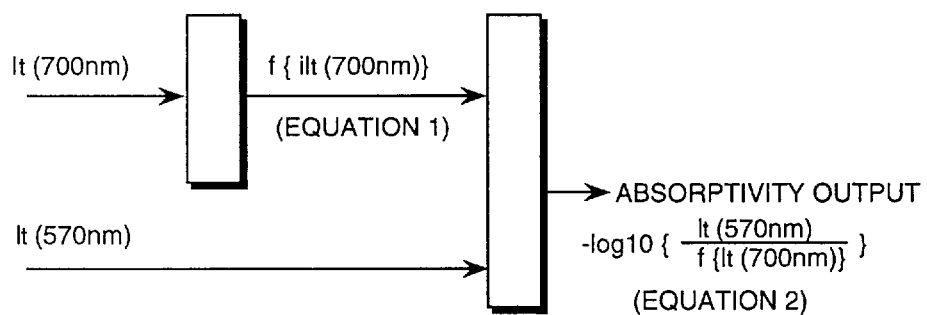
FIG. 1 is a block diagram of absorptivity calculation.

After that, an absorptivity is output using a transform function having these coefficients, as shown in FIG. 1.

The quadratic equation (Equation 4) may be changed to the linear equation (Equation 3) or a linear equation passing on the point of origin (a proportional equation).

② A case of selecting refractive index change:

While voltage of the light source is kept constant, the buffer solution 1 is fed by the pump 7 and the ninhydrin buffer solution 17 is fed by the pump 12. The flow rates at that time are set to values of a latest set analysis condition. When the flow rates are changed, this function is stared to be operated once the analysis condition is changed. Then a plotted graph is formed as similar to the case of light source voltage change, and regression coefficients are obtained, and the operation is completed.

③ A case of selecting absorptivity change:

While voltage of the light source is kept constant, the buffer solution 1 is fed by the pump 7 and the ninhydrin reagent 11 is fed by the pump 12. The flow rates at that time are set to values of a latest set analysis condition. When the flow rates are changed, this function is stared to be operated once the analysis condition is changed. Then a plotted graph is formed as similar to the case of light source voltage change, and regression coefficients are obtained, and the operation is completed. In order to bring the refractive index change close to an actual analysis condition, water or a buffer solution not having absorptivity may be fed instead of the ninhydrin reagent 11.

The present embodiment has the following effects.

(1) Change in an absorptivity caused by change in light intensity of a light source can be suppressed, and it is possible to perform measurement stably for a long time.

(2) In the past, several hours of warming-up from switching-on a light source to attaining a necessary stable level has been required. The warming-up can be substantially shortened, and consequently analysis can be stared within a short period from switching-on the light source.

(3) In the detector, change in measured values due to difference in light intensity of each light source can be suppressed.

As having been described above, according to the present invention, accuracy of detecting absorptivity can be maintained even if change of intensity of a light source occurs.

What is claimed is:

1. An absorptivity detecting apparatus comprising:
   a separation column for separating sample solution,
   a flow cell for flowing said sample solution separated by said separation column,
   a light source for emitting light containing a reference wavelength and a sample measurement wavelength;
   means for separating said reference wavelength and said sample measurement wavelength after passing through said sample solution flowing in said flow cell,
   a detector for detecting said reference wavelength and said sample measurement wavelength upon separation thereof by said means for separating;
   a correction value output means for outputting a correction value corresponding to an intensive change ratio of the reference wavelength and an intensity change ratio of the measurement wavelength caused by change in light intensity of said light source; and
   an absorptivity detecting means for detecting an absorptivity of said sample solution based on said correction value, a detected value of said reference wavelength and a detected value of said sample measurement wavelength.

2. An absorptivity detecting apparatus according to claim 1, wherein an intensity of incident light in said sample measurement wavelength is estimated using the detected value of said reference wavelength.

3. An absorptivity detecting apparatus according to claim 1, wherein said correction value is obtained based on Planck's black body radiation law.

4. An absorptivity detecting apparatus according to claim 1, wherein detection of said reference wavelength and of said sample measurement wavelength is performed by moving said sample solution.

5. An absorptivity detecting apparatus according to claim 1, wherein detection of said reference wavelength and of said sample measurement wavelength is performed while said sample solution is moved.

6. An absorptivity detecting apparatus according to claim 1, wherein a reaction unit for reacting with a reaction agent is arranged in a flow passage between said separation column and said flow cell.

7. An absorptivity detecting method comprising:
   separating sample solution in a separation column;
   flowing said sample solution separated by said separation column through a flow cell;
   emitting from a light source light containing a reference wavelength and a sample measurement wavelength;
   separating said reference wavelength and said sample measurement wavelength after passing through said sample solution flowing in said flow cell;
   detecting said reference wavelength and said sample measurement wavelength upon separation thereof;
   outputting a correction value corresponding to an intensity change ratio of the reference wavelength and an intensity change ratio of the measurement wavelength caused by change in light intensity of said light source; and
   detecting an absorptivity of said sample solution based on said correction value, a detected value of said reference wavelength and a detected value of said sample measurement wavelength.

* * * * *